US005750748A

United States Patent [19]

Boutique et al.

[11] Patent Number: 5,750,748
[45] Date of Patent: May 12, 1998

[54] N-ALKYL POLYHYDROXY FATTY ACID AMIDE COMPOSITIONS AND THEIR METHOD OF SYNTHESIS

[75] Inventors: Jean-Pol Boutique, Ernage; Patrick Firmin A. Delplancke, Zwevegem, both of Belgium

[73] Assignee: The Procter & Gamble Company, Cincinnati, Ohio

[21] Appl. No.: 633,745

[22] PCT Filed: Nov. 14, 1994

[86] PCT No.: PCT/US94/13022

§ 371 Date: Apr. 19, 1996

§ 102(e) Date: Apr. 19, 1996

[87] PCT Pub. No.: WO95/14754

PCT Pub. Date: Jun. 1, 1995

[30] Foreign Application Priority Data

Nov. 26, 1993 [EP] European Pat. Off. .............. 93203307

[51] Int. Cl.$^6$ .............. C07C 231/02; C11C 3/00; C11D 3/32
[52] U.S. Cl. .............. 554/66; 554/66; 510/276; 510/313; 510/326; 510/342; 510/499; 510/501; 510/502; 510/433
[58] Field of Search .............. 510/276, 313, 510/326, 342, 499, 501, 502, 433; 554/66

[56] References Cited

U.S. PATENT DOCUMENTS

| | | | |
|---|---|---|---|
| 2,703,798 | 3/1955 | Schwartz | 260/211 |
| 5,174,927 | 12/1992 | Honsa | 252/543 |
| 5,188,769 | 2/1993 | Connor et al. | 252/548 |
| 5,194,639 | 3/1993 | Connor et al. | 554/66 |
| 5,283,009 | 2/1994 | Speckman et al. | 252/548 |
| 5,298,636 | 3/1994 | Connor et al. | 554/70 |
| 5,318,728 | 6/1994 | Surutzidis et al. | 252/548 |
| 5,334,764 | 8/1994 | Scheibel et al. | 564/487 |
| 5,338,486 | 8/1994 | Connor et al. | 252/357 |
| 5,338,487 | 8/1994 | Connor et al. | 252/357 |

FOREIGN PATENT DOCUMENTS

| | | | |
|---|---|---|---|
| 3-246265 | 11/1991 | Japan | C07C 233/18 |
| 92/05764 | 4/1992 | WIPO . | |
| WO 9205764 | 4/1992 | WIPO | A61K 7/06 |
| WO 9206150 | 4/1992 | WIPO | C11D 3/00 |
| WO 9206151 | 4/1992 | WIPO | C11D 1/52 |
| WO 9206171 | 4/1992 | WIPO | C11D 17/00 |

*Primary Examiner*—Douglas J. McGinty
*Assistant Examiner*—Charles Boyer
*Attorney, Agent, or Firm*—Brian M. Bolam; Kim William Zerby; Jerry J. Yetter

[57] ABSTRACT

A process for the preparation of a surfactant composition comprising N-methyl polyhydroxy fatty acid amide and N-alkyl (C3-C8) polyhydroxy fatty acid amide comprises mixing N-methyl polyhydroxy fatty acid amine and N-alkyl (C3-C8) polyhydroxy fatty acid amine to form a mixture. The mixture is reacted with a fatty acid ester reactant in the presence of a base catalyst and, optionally, in the presence of a reaction solvent. Unreacted N-alkoxyamino polyol is acylated with an acid anhydride at a temperature in the range of from 50° C. to 85° C. The weight ratio of N-methyl polyhydroxy fatty acid amide to N-alkyl (C3-C8) polyhydroxy fatty acid amide in the surfactant composition is from 25:1 to 1:1.

7 Claims, No Drawings

N-ALKYL POLYHYDROXY FATTY ACID AMIDE COMPOSITIONS AND THEIR METHOD OF SYNTHESIS

FIELD OF THE INVENTION

The present invention relates to certain mixtures of N-alkyl polyhydroxy fatty acid amide detersive surfactants and their method of synthesis.

BACKGROUND OF THE INVENTION

The formulation of detergent compositions presents a considerable challenge, since effective compositions are required to remove a variety of soils and stains from diverse substrates. In particular, the removal of greasy/oily soils quickly and efficiently can be problematic. While a review of the literature would seem to indicate that a wide selection of surfactants is available to the detergent manufacturer, the reality is that many such materials are specialty chemicals which are not suitable in low unit cost items such as home-use detergent compositions. The fact remains that most home-use detergents still comprise one or more of the conventional ethoxylated nonionic and sulfated or sulfonated anionic surfactants, presumably due to economic considerations.

The challenge to the detergent manufacturer seeking improved fabric cleaning has been increased by various environmental factors. For example, some nonbiodegradable ingredients have fallen into disfavor. Effective phosphate builders have been banned by legislation in many countries. Moreover, many surfactants are often available only from nonrenewable resources such as petrochemicals. Accordingly, the detergent manufacturer is quite limited in the selection of surfactants which are effective cleaners, biodegradable and, to the extent possible, available from renewable resources such as natural fats and oils, rather than petrochemicals.

Considerable attention has lately been directed to nonionic surfactants which can be prepared by using mainly renewable resources, such as fatty esters and sugars. One such class of surfactants includes the N-alkyl polyhydroxy fatty acid amides. Moreover, the combination of such nonionic surfactants with conventional anionic surfactants such as the alkyl sulfates, alkyl benzene sulfonates, alkyl ether sulfates, and the like has also been studied. Indeed, substantial success in the formulation of dishwashing compositions has recently been achieved using the N-alkyl polyhydroxy fatty acid amides. However, even these superior surfactants do suffer from some drawbacks. For example, their solubility is not as high as might be desired for optimal formulations and this is exacerbated at chain lengths of about $C_{16}$ and above. At high concentrations in water they can be difficult to handle, store and pump, so additives must be employed in manufacturing plants to control their viscosity and maintain their fluidity.

A suitable method for the manufacture of N-alkyl polyhydroxy fatty acid amides having desirable low color and little or no contamination with cyclized by-products, carried out in the presence of organic hydroxy solvents, is disclosed in U.S. Pat. No. 5,194,639, Connor, Scheibel and Severson, issued Mar. 16, 1993.

In order to prevent gelling or solidification of the liquid fatty acid amides, it has generally been found to be necessary to store them at elevated temperatures, and/or to add substantial quantities of organic solvents mentioned in U.S. Pat. No. 5,194,639.

It has now been discovered that certain mixtures of N-alkyl polyhydroxy fatty acid amides can be prepared using low levels of organic solvents, and can be stored at ambient temperatures.

Accordingly, the present invention provides new, highly soluble, highly detersive surfactants which have the addtional advantage that they can be prepared in an efficient and effective manner with reduced need for solvents, and which can be stored in the liquid state at ambient temperatures.

BACKGROUND ART

Japanese Kokai HEI 3[1991]-246265 Osamu Tachizawa, U.S. Pat. Nos. 5,194,639, 5,174,927 and 5,188,769 and WO 9,206,171, 9,206,151, 9,206,150 and 9,205,764 relate to various polyhydroxy fatty acid amide surfactants and uses thereof.

SUMMARY OF THE INVENTION

The present invention concerns aqueous surfactant composition comprising poly hydroxy fatty acid amides of the formula (A):

wherein R2 is C11–C19 alkyl, alkenyl or mixtures thereof; Z is a polyhydroxyhydrocarbyl moiety having a linear hydrocarbyl chain with at least 3 hydroxyls directly connected to the chain; and in a part of the total amide surfactant (a) R1 is a methyl group and in the remainder of the total amide surfactant (b) R1 is an alkyl group with from 3 to 8 carbon atoms;

said composition further comprising (c) from 0% to 15% by weight of an organic solvent;

wherein the ratio of N-methyl poly hydroxy fatty acid amide (a) to N-alkyl (C3–C8) polyhydroxy fatty acid amide (b), is from 25:1 to 1:1.

In a preferred embodiment of the present invention, the surfactant composition is prepared by mixing N-methyl poly hydroxy fatty acid amine and N-propyl poly hydroxy fatty acid amine, and reacting said mixture with a fatty acid ester reactant in the presence of a base catalyst and, preferably, in the presence of a reaction solvent.

DETAILED DESCRIPTION OF THE INVENTION

The present invention provides an aqueous surfactant composition which preferably comprises at least 30% by weight of N-methyl poly hydroxy fatty acid amide and which remains as a homogeneous liquid for at least 1 week when stored at 25° C. Preferably the composition comprises at least 40% by weight of polyhydroxy fatty acid amides (in total)

In addition the aqueous surfactant composition preferably comprises (a) N-methyl poly hydroxy fatty acid amide;

(b) N-alkyl poly hydroxy fatty acid amide, having an alkyl chain length of from 3 to 8 carbon atoms;

wherein (a) and (b) are both amides of the formula (A), and furthermore the weight ratio of (a) to (b) is from 15:1 to 2:1, preferably from 15:1 to 5:1.

The surfactants of formula (A) are preferably based on the following groups: where R2—CO—N< is preferably selected from the group consisting of cocoamide, stearamide, oleamide, lauramide, myristamide, capricamide, palmitamide, tallowamide and mixtures of these, and Z is a glycityl moiety.

R1 preferably consists of methyl (a) and propyl (b) groups.

Any suitable organic solvent may be used, such as methanol, ethanol, propanol, iso-propanol, the butanols, glycerol, 1,2-propylene glycol, and 1,3-propylene glycol. Organic solvents are preferably used at a level of less than 5% by weight of the composition.

The most preferred compositions of the present invention comprise:

(a) at least 40% by weight of N-methyl glucamide
(b) from 2.5is to 15% by weight of N-propyl glucamide
(c) from 2% to 8% by weight of propylene glycol The following defines the terms used herein.

By "low-color" herein is meant a N-alkyl polyhydroxy fatty acid amide reaction product which is substantially white or light beige. On the standard Gardner scale, a color in the range of 0–4, preferably 0–2, most preferably 0, is secured.

By "cyclized by-products" herein is meant contaminants which undesirably form during the synthesis by internal cyclization of the polyol structure (e.g., glycityl) of the N-alkyl polyhydroxy fatty acid amides herein, presumably by a dehydration reaction. The term "cyclized by-products" does not refer to natural cyclic structures, such as those which may be present in di- and higher saccharide reducing sugars such as maltose. The process of this invention provides N-alkyl polyhydroxy fatty acid amides which are substantially free, i.e., which contain less than 10% preferably 1% or less, of undesirable "cyclized by-products".

By "ester amides" herein is meant N-alkyl polyhydroxy fatty acid amides whose polyol units have undesirably undergone a further reaction with the fatty acid ester reactant to form one or more fatty ester linkages. The process of this invention provides N-alkyl polyhydroxy fatty acid amides which are substantially free, i.e., which contain less than 10%, preferably less than 5%, most preferably 1% or less, of such ester-amides.

It is to be understood that the polyhydroxy amines used herein can be derived from an alkoxy amine and any desired reducing sugar, such as glucose (preferred), xylose, maltose, fructose, and the like.

In a second aspect of the invention, a process is provided in which a mixture of amines is reacted with esters in the presence of a base catalyst.

The process herein is conducted under the following conditions.

Preferably, the base catalyst used in the process is an alkoxide material, especially sodium methoxide. The fatty acid "ester" can be a $C_8$–$C_{22}$ fatty acid alkyl ester or, for the sake of economy, a $C_8$–$C_{22}$ fatty acid mono-, di- or triglyceride ester. Thus, natural plant oils such as palm oil, soy oil, coconut oil, palm kernel oil, canola oil and the like, can be used in the process.

In a preferred mode of the reaction, the fatty acid ester is a $C_{11}$–$C_{19}$ fatty acid methyl ester and the N-alkyl polyhydroxy amine reactants are N-methyl glucamine and N-propyl glucamine.

In order to provide low-colour products, and to minimize ester amide or cyclic by-products formed by the polyol substituent, the process herein is preferably conducted at a temperature below about 170° C., most preferably in the range from about 140° C. to about 70° C. If desired, any unreacted N-alkoxyamino polyol remaining in the product can be acylated (50° C.–85° C.) with an acid anhydride, e.g., acetic anhydride, maleic anhydride, or the like, in water to minimize the overall level of such residual amines in the product. Residual sources of straight chain fatty acids, which can suppress suds, can be depleted by reaction with, for example, monoethanolamine (50° C.–85° C.).

In a most preferred mode of the reaction, a reaction solvent is present. Suitable reaction solvents include C1–C4 alcohol, ethylene glycol, alkoxylated alcohol, or mixtures thereof. Propylene glycol is most preferred.

Optional Components

Additional components which contribute to the prevention of gelling, precipitation or solidification may, optionally, be included in the compositions of the present invention. Such components include carboxylate and borate funtional materials.

Useful carboxylate functional materials including citrates, oxydisuccinates, tartrates, tartrate monosuccinate, tartrate disuccinate, gluconate and saccharate have been disclosed in the Applicants co-pending application no. PCT/US9302066, filed on 8th March, 1993.

Useful borate functional materials include boric acid or its salts, such as metaborate or tetraborate, and borax. These have been disclosed in the Applicants co-pending Application EP92870164.8, filed on 13th Oct. 1992.

EXAMPLE

The following surfactant compositions were prepared:

| | A | B | C | D | E |
|---|---|---|---|---|---|
| C12 N-methyl glucamide | 30 | 30 | 30 | 40 | 50 |
| C12 N-propyl glucamide | 15 | — | — | — | 12 |
| C12 N-butyl glucamide | — | 15 | 15 | 2 | — |
| Ethanol | — | — | — | 2 | 3 |
| 1,2 Propanediol | 5 | — | 5 | 8 | 7 |
| Water | | up to 100 parts | | | |

All examples stay clear, transparent liquids after 1 week storage at 25° C.

The compositions of Examples A to E were first prepared by mixing appropriate quantities of N-methyl glucamide, N-propyl or N-butyl glucamide, organic solvent and water.

The compositions of Examples A to E can also be prepared by mixing the appropriate proportions of N-methyl glucamine with either N-propyl glucamine (Examples A and E) or N-butyl glucamine (Examples B, C and D). The mixture of glucamine was reacted with C12 fatty acid methyl ester in the presence of sodium methoxide base catalyst and 1,2 propane diol where present (Examples A, C, D and E) at a temperature of 80° C. After completion of the amidation reaction the glucamides were diluted with water and ethanol added were present (Examples D and E) to give the finished compositions.

We claim:

1. A process for the preparation of a surfactant composition comprising N-methyl polyhydroxy fatty acid amide and N-alkyl (C3–C8) polyhydroxy fatty acid amide comprising the steps of:

(i) mixing N-methyl polyhydroxy fatty acid amine and N-alkyl (C3–C8) polyhydroxy fatty acid amine to form a mixture, (ii) reacting said mixture with a fatty acid ester reactant in the presence of a base catalyst and, optionally, in the presence of a reaction solvent, and (iii) acylating unreacted N-alkoxyamino polyol with an acid anhydride at a temperature in the range of from 50° C. to 85° C.;

wherein the weight ratio of N-methyl polyhydroxy fatty acid amide to N-alkyl (C3–C8) polyhydroxy fatty acid amide is from 25:1 to 1:1.

2. A process according to claim 1 wherein the base catalyst is an alkoxide material.

3. A process according to claim 1 wherein the reaction of the mixture with the fatty acid ester reactant is maintained at a temperature between 70° C. to 140° C.

4. A process according to claim 1 wherein the reaction solvent comprises propylene glycol.

5. A process according to claim 1, further comprising the step of reacting residual sources of straight chain fatty acids with monoethanolamine at a temperature in the range of from 50° C. to 85° C.

6. A process according to claim 1 wherein the N-alkyl (C3–C8) polyhydroxy fatty acid amine is selected from the group consisting of N-propyl glucamine, N-butyl glucamine and mixtures thereof.

7. A process according to claim 1 wherein the N-methyl polyhydroxy fatty acid amine comprises N-methyl glucamine and the N-alkyl (C3–C8) polyhydroxy fatty acid amine is selected from the group consisting of N-propyl glucamine, N-butyl glucamine and mixtures thereof; and further wherein the surfactant composition comprises from 30% to 50% of a N-methyl glucamide, 2 % to 15 % of a N-alkyl glucamide selected from the group consisting of N-propyl glucamides, N-butyl glucamides and mixtures thereof, and from 2% to 8% solvent.

* * * * *